US00PP16816P2

(12) United States Plant Patent
Wain

(10) Patent No.: US PP16,816 P2
(45) Date of Patent: Jul. 18, 2006

(54) ***CHRYSANTHEMUM* PLANT NAMED 'YOBRIANNA'**

(50) Latin Name: *Chrysanthemum×morifolium*
Varietal Denomination: Yobrianna

(75) Inventor: Peter Wain, Southampton (GB)

(73) Assignee: Yoder Brothers, Inc., Barberton, OH (US)

( * ) Notice: Subject to any disclaimer, the term of this patent is extended or adjusted under 35 U.S.C. 154(b) by 269 days.

(21) Appl. No.: 10/937,765

(22) Filed: Sep. 8, 2004

(51) Int. Cl.
*A01H 5/00* (2006.01)

(52) U.S. Cl. ..... Plt./294

(58) Field of Classification Search ..... Plt./294
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yobrianna', characterized by its upright, outwardly spreading and rounded plant habit; freely branching habit; dense and full appearance; uniform and freely flowering habit; small daisy-type inflorescences with elongated oblong-shaped ray florets; white-colored ray florets and bright yellow-colored disc florets; natural season flowering in mid-October in the Northern Hemisphere; and good garden performance.

2 Drawing Sheets

Botanical classification/cultivar designation: *Chrysanthemum×morifolium* cultivar Yobrianna.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yobrianna'.

The new cultivar is a product of a planned breeding program conducted by the Inventor in Fareham, Hants, United Kingdom. The objective of the breeding program is to create new garden-type *Chrysanthemum* cultivars having inflorescences with desirable inforescence forms, attractive floret coloration and good garden performance.

The new *Chrysanthemum* originated from a cross-pollination made in March, 1998 in Fareham, Hants, United Kingdon, of the *Chrysanthemum×morifolium* cultivar Pidoul, disclosed in U.S. Plant Pat. No. 10,218, as the female, or seed, parent with a proprietary selection of *Chrysanthemum×morifolium* identified as code number G137A1, not patented, as the male, or pollen, parent. The new *Chrysanthemum* was discovered and selected by the Inventor as a single flowering plant within the progeny of the stated cross-pollination grown in a controlled environment in Fareham, Hants, United Kingdom in September, 1998. The selection of this plant was based on its desirable inflorescence form, attractive floret coloration and good garden performance.

Asexual reproduction of the new cultivar by terminal vegetative cuttings in a controlled environment in Fareham, Hants, United Kingdom since December, 1998, has shown that the unique features of this new *Chrysanthemum* are stable and reproduced true to type in successive generations.

SUMMARY OF THE INVENTION

The cultivar Yobrianna has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yobrianna'. These characteristics in combinaton distinguish 'Yobrianna' as a new and distinct cultivar of *Chrysanthemum:*

1. Upright, outwardly spreading and rounded plant habit.
2. Freely branching habit; dense and full plants.
3. Uniform and freely flowering habit.
4. Small daisy-type inflorescences with elongated oblong-shaped ray florets.
5. White-colored ray florets and bright yellow-colored disc florets.
6. Natural season flowering in mid-October in the Northern Hemisphere.
7. Good garden performance.

In side-by-side comparisons conducted in Fareham, Hants, United Kingdom, plants of the new *Chrysanthemum* differed from plants of the female parent, the cultivar Pidoul, in the following characteristics:

1. Plants of the new *Chrysanthemum* were larger than plants of the cultivar Pidoul.
2. Plants of the new *Chrysanthemum* flowered later than plants of the cultivar Pidoul.

In side-by-side comparisons conducted in Fareham, Hants, United Kingdom, plants of the new *Chrysanthemum* differed from plants of the male parent, the proprietary selection identified as code number G137A1, in the following characteristics:

1. Inflorescences of plants of the new *Chrysanthemum* had fewer ray florets than inflorescences of plants of the male parent selection.
2. Plants of the new *Chrysanthemum* and the male parent selection differed in ray floret coloration as plants of the male parent selection had creamy white-colored ray florets.

Plants of the new *Chrysanthemum* can be compared to plants of the *Chrysanthemum* cultivar Shepherd, disclosed in U.S. Plant Pat. No. 13,371. In side-by-side comparisons conducted in Alva, Fla. under natural season conditions, plants of the new *Chrysanthemum* differed from plants of the cultivar Shepherd in the following characteristics:

1. Plants of the new *Chrysanthemum* were larger than plants of the cultivar Shepherd.
2. Plants of the new *Chrysanthemum* had slightly smaller inflorescences than plants of the cultivar Shepherd.
3. Plants of the new *Chrysanthemum* flowered about two weeks later than plants of the cultivar Shepherd.

Plants of the new *Chrysanthemum* can also be compared to plants of the *Chrysanthemum* cultivar Papiro, disclosed in U.S. Plant Pat. No. 12,998. In side-by-side comparisons conducted in Alva, Fla. under natural season conditions, plants of the new *Chrysanthemum* differed from plants of the cultivar Papiro in the following characteristics:

1. Plants of the new *Chrysanthemum* were larger and had a more rounded crown than plants of the cultivar Papiro.
2. Plants of the new *Chrysanthemum* had larger inflorescences than plants of the cultivar Papiro.
3. Plants of the new *Chrysanthemum* flowered about 10 to 14 days earlier than plants of the cultivar Papiro.
4. Plants of the new *Chrysanthemum* and the cultivar Papiro differed in ray floret coloration as plants of the cultivar Papiro had creamy white-colored ray florets.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yobrianna' grown in a container.

The photograph on the second sheet comprises a close-up view of typical inflorescences of the cultivar 'Yobrianna'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Yobrianna.

Commercial classification: Daisy-type garden *Chrysanthemum*.

Parentage:

*Female, or seed, parent.*—*Chrysanthemum×morifolium* cultivar Pidoul, disclosed in U.S. Plant Pat. No. 10,218.

*Male, or pollen, parent.*—Proprietary selection of *Chrysanthemum×morifolium* identified as code number G137A1, not patented.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous daisy-type garden *Chrysanthemum*. Inverted triangle with mounded crown; rounded plant habit. Stems initially upright, then outwardly spreading. Freely branching with lateral branches potentially developing at every node. Moderately vigorous to vigorous.

*Plant height.*—About 17.5 cm.

*Plant diameter.*—About 35 cm.

*Lateral branches.*—Length: About 19 cm. Diameter: About 5 mm. Internode length: About 1.4 cm. Strength: Strong. Texture: Pubescent. Color: Close to 144A.

*Foliage description.*—Leaf arrangement: Alternate. Length: About 4.1 cm. Width: About 2.3 cm. Apex: Mucronate. Base: Attenuate. Margin: Palmately and deeply lobed; sinuses mostly divergent. Texture, upper and lower surfaces: Pubescent. Color: Developing foliage, upper surface: More green than 147A. Developing foliage, lower surface: More green than 147B. Fully expanded foliage, upper surface: More green than 147A. Fully expanded foliage, lower surface: Close to 147B. Venation, upper surface: Close to 147A to 147B. Venation, lower surface: Close to 147B. Petiole: Length: About 1.3 cm. Diameter: About 2.5 mm. Texture, upper and lower surfaces: Pubescent. Color, upper surface: Close to 146A to 146B. Color, lower surface: Close to 146B.

Inflorescence description:

*Appearance.*—Daisy-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences slightly cupped. Uniform and freely flowering; about 35 inflorescences develop per lateral branch. Inflorescences persistent. Inflorescences not fragrant.

*Flowering response.*—Under natural season conditions, plants flower in mid-October in the Northern Hemisphere.

*Inflorescence bud (before showing color).*—Height: About 4 mm. Diameter: About 6 mm. Shape: Oblate. Color (lower surface of phyllaries): Close to 146A.

*Inflorescence size.*—Diameter: About 2.8 cm. Depth (height): About 1 cm. Disc diameter: About 1 cm. Receptacle diameter: About 4 mm. Receptacle height: About 5 mm.

*Ray florets.*—Shape: Elongated oblong. Length: About 1.3 cm. Corolla tube length: About 4 mm. Width: About 4 mm. Apex: Emarginate to acute. Margin:

Fused. Texture: Smooth, glabrous; satiny. Surface: Concave to flat. Orientation: Initially upright, then somewhat upright. Number of ray florets per inflorescence: About 30 in about on to two whorls. Color: When opening and fully opened, upper surface: Close to 155D. When opening and fully opened, lower surface: Close to 155D.

*Disc florets.*—Shape: Tubular; apex dentate, five-pointed. Length: About 5 mm. Width, apex: About 1.5 mm. Width, base: About 1 mm. Number of disc florets per inflorescence: Numerous. Color: Immature: Close to 9A to 12A. Mature: Apex: Close to 12A. Mid-section: Close to 144C. Base: Close to 155D.

*Phyllaries.*—Quantity per inflorescence: About 18. Length: About 6 mm. Width: About 3 mm. Shape: Deltoid. Apex: Acute. Base: Truncate, fused. Margin: Entire. Texture, upper surface: Smooth, waxy. Texture, lower surface: Pubescent. Color, upper surface: Close to 144A. Color, lower surface: Close to 146A.

*Peduncle.*—Length: First peduncle: About 6.6 cm. Fourth peduncle: About 8.5 cm. Seventh peduncle: About 12.6 cm. Diameter: About 2 mm. Strength: Strong. Aspect: About 30 to 45° from vertical. Texture: Pubescent. Color: Close to 144A.

*Reproductive organs.*—Androecium: Present on disc florets only. Anther color: Close to 9A to 12A. Pollen: None observed. Gynoeicum: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed:

1. A new and distinct cultivar of *Chrysanthemum* plant named 'Yobrianna', as illustrated and described.

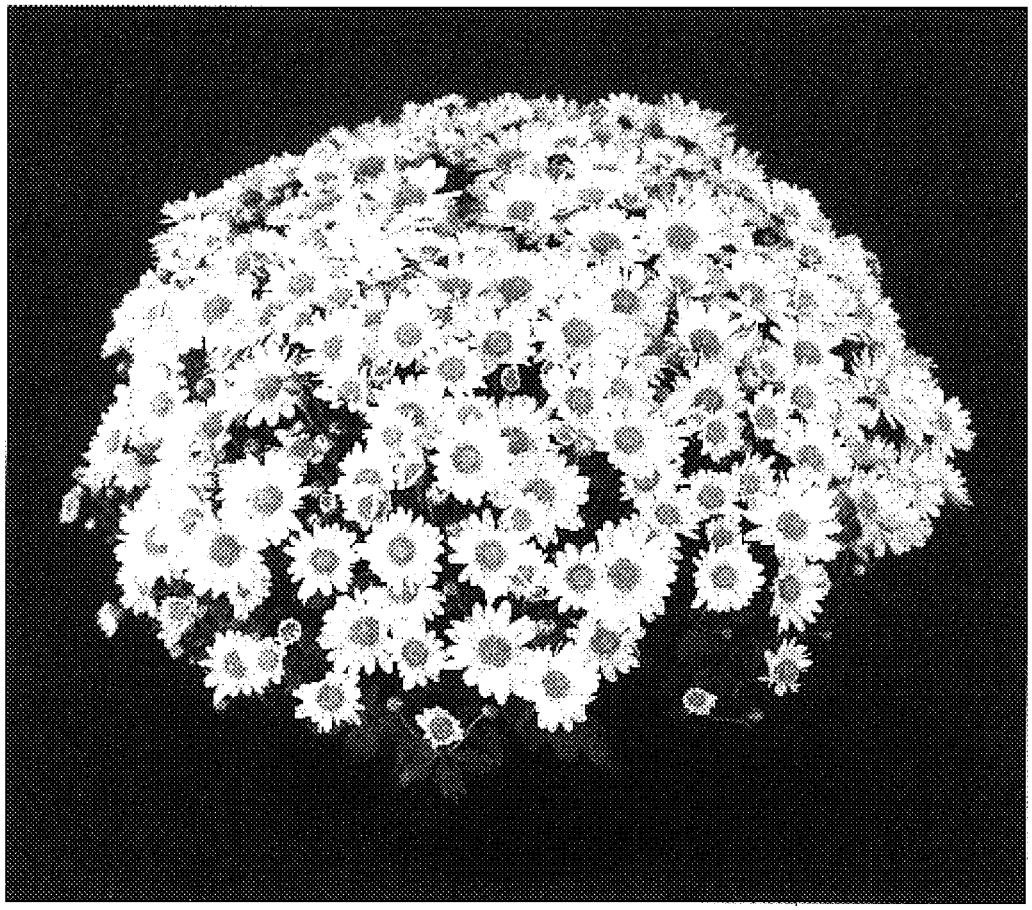

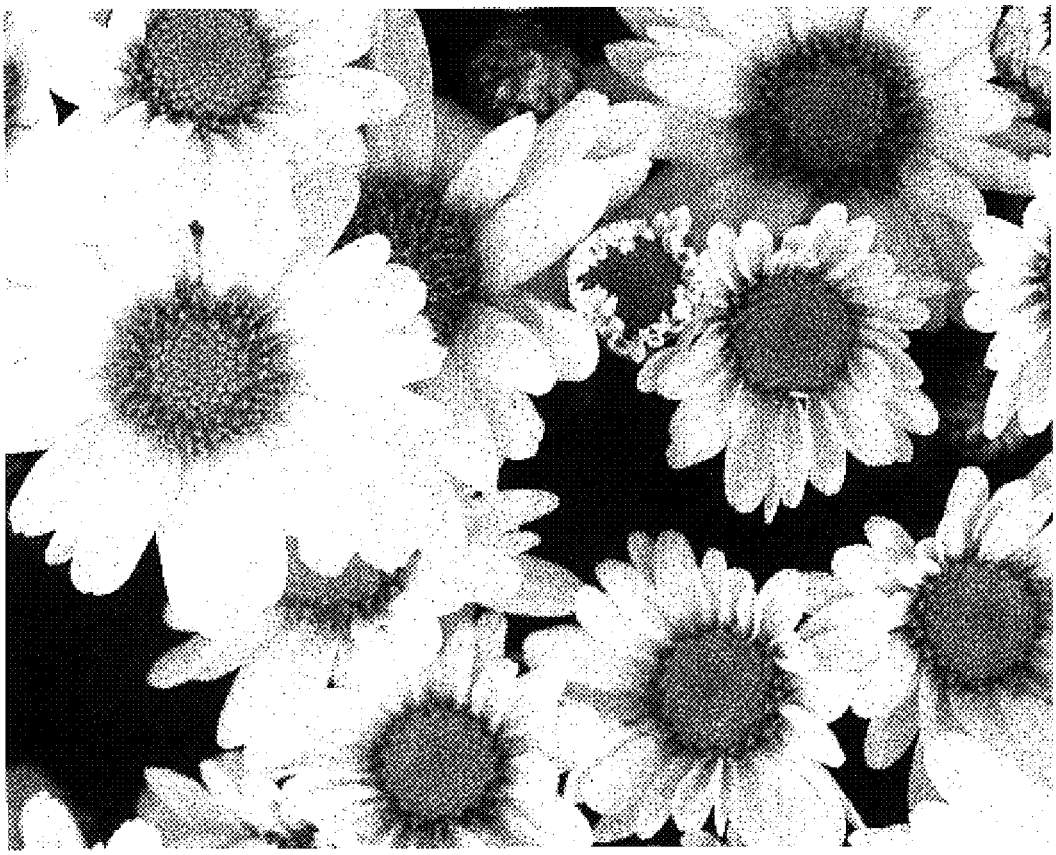

* * * * *